United States Patent
Folan (10) Patent No.: US 6,423,336 B1
(45) Date of Patent: Jul. 23, 2002

(54) CHEWING GUMS AND METHOD OF MANUFACTURING THE SAME

(76) Inventor: Michael Anthony Folan, Westgate, Lough Eske, Donegal Town (IE)

( * ) Notice: Subject to any disclaimer, the term of this patent is extended or adjusted under 35 U.S.C. 154(b) by 0 days.

(21) Appl. No.: 09/308,101
(22) PCT Filed: Nov. 4, 1997
(86) PCT No.: PCT/IE97/00073
§ 371 (c)(1), (2), (4) Date: Jun. 24, 1999
(87) PCT Pub. No.: WO98/19558
PCT Pub. Date: May 14, 1998

(30) Foreign Application Priority Data

Nov. 4, 1997 (IE) .................................................. 960771

(51) Int. Cl.7 ........................... A61K 9/68; A61K 35/78; A61K 38/00; A23G 3/30
(52) U.S. Cl. ...................... 424/440; 424/48; 424/195.1; 426/5; 514/2
(58) Field of Search ....................... 424/48, 440, 195.1; 426/5; 514/2

(56) References Cited

U.S. PATENT DOCUMENTS

| | | | |
|---|---|---|---|
| 2,973,273 A | * | 2/1961 | Curtiss ........................... 426/5 |
| 4,000,321 A | | 12/1976 | Mochizuki et al. |
| 4,301,178 A | | 11/1981 | Witzel et al. |
| 5,178,850 A | | 1/1993 | DuRoss |

FOREIGN PATENT DOCUMENTS

| | | |
|---|---|---|
| EP | 0288909 | 2/1988 |
| WO | 9308699 | 5/1993 |
| WO | 9603111 | 8/1996 |

OTHER PUBLICATIONS

FSTA Abstract, AN 93(01):J0114, 1993, Kanda et al.*
Margrethe Rømer Rassing, Chewing gum as a drug delivery system, (1994) p. 89–121.

* cited by examiner

Primary Examiner—Russell Travers
Assistant Examiner—Shengjun Wang
(74) Attorney, Agent, or Firm—Fulbright & Jaworski L.L.P.

(57) ABSTRACT

Chewing gum are obtained by entrapping a liquid within a mass of gum, blast freezing the gum and entrapped liquid, and increasing the temperature to just below the melting point of the liquid, causing the liquid crystals to anneal. By manipulating the size and/or morphology of the frozen liquid crystals, one can thereby manipulate the internal structure of the gum. Optionally, the liquid can contain a drug in solution. If the solvent is then removed, the drug is left in the interstices of the gum. The rate of release of the drug from the gum is thus determined by the distribution of the drug within the gum arising from the annealing step. This method of manufacturing a chewing gum avoids the use of elevated temperatures, and is particularly suitable for entrapping thermolabile substances.

25 Claims, 4 Drawing Sheets

CHEWING GUMS AND METHOD OF MANUFACTURING THE SAME

This application is a 371 of PCT/IE97/00073, filed Nov. 4, 1997, which claim the foreign priority of Germany 960771, filed Nov. 4, 1997.

TECHNICAL FIELD

This invention relates to chewing gums and in particular to their use in the delivery of active ingredients, including liquid solutions of active ingredients, thermolabile active ingredients in solid or liquid form and homeopathic medicines.

BACKGROUND ART

The use of chewing gum as a drug delivery vehicle is well known and under extensive investigation by many researchers (see, for example, "Chewing gum as a drug delivery system", Margrethe Romer Rassing, *Advanced Drug Delivery Reviews,* 13, 89–121 (1994)). Apart from the fact that chewing gum offers a convenient and easily used vehicle for active ingredient administration, it presents additional features of pharmacological importance including the fact that absorption of active ingredients through the oral mucosa avoids hepatic first pass metabolism, and may therefore offer an opportunity to reduce therapeutic dose requirements.

The primary disadvantage of chewing gum is a difficulty in regulating the total dose administered. In many cases it is impossible to formulate gum such that the total dose contained is released and made available for absorption.

While buccal absorption of active ingredients avoids liver metabolism, the act of chewing produces saliva which necessitates swallowing and there is no way of regulating the amount of active ingredient which is swallowed and the amount absorbed through the buccal mucosa. Furthermore, active ingredients which are poorly water-soluble are not easily absorbed when present in chewing gum in solid form.

Another problem is thermal stability: the industry standard method of formulating any chewing gum involves a hot melt process in which the temperature of the gum base (to which active ingredients, flavours and excipients are added as a dry powder) may be of the order of 80° C. Thermolabile active ingredients are denatured by the high processing temperatures and thus cannot be formulated for delivery using the industry standard process technology.

A solution to this problem has been proposed which avoids the high temperatures of the hot melt process. By freezing the gum it can be comminuted by grinding, and then an active ingredient can be added in powdered form. The mixture of powdered active ingredient and frozen gum particles can be compressed together and thawed. Processes of this type are disclosed in: U.S. Pat. No. 4,000,321, U.S. Pat. No. 4,161,544 and U.S. Pat. No. 4,737,366.

WO 96/03111 discloses details of comminution of gum to a powdered form followed by blending with liquid ingredients, before compression to the form of tablets which are then subsequently dried by hot air.

Despite the disadvantages, there are many suitable active ingredient candidates some of which are already available in the market in chewing gum form. These active ingredients include nicotine, anti-microbials for local oral infection, fluoride gums for prevention of dental caries, vitamins and some functional foods. The common feature of all commercial products is that they are intended for local oral application of the active ingredient and, like ointments or other conventional topical medicaments, the total dose administered is not critical to the therapeutic value.

The delivery of liquids presents its own problems, particularly where aqueous solutions are involved. A major problem in entrapping water in chewing gums is that water (and liquids such as water/ethanol solutions which are often used as a base for homeopathic dilutions) are not compatible with conventional chewing gum processing. There is no point in enclosing a discrete volume of water en masse in a gum envelope because the volume bursts out in the first bite. So a problem exists in finding some way of dispersing the aqueous solution in the gum such that it is released slowly over a period of about twenty minutes, without subjecting the active ingredient to some incompatible conditions such as extreme heat, shearing, electromagnetic forces or chemical manipulation.

If a liquid must be encapsulated, other methods can be used, such as using a resin which holds a polar liquid therein by charge attraction (such as the nicotine gums marketed by Kabi Pharmacia as "Nicorette"); or the liquid can be encapsulated in liposomes (also referred to as nanospheres/microspheres depending on size) and these particles can be entrapped in a gum in much the same way as with a powder. The use of "micro-sponges", containing encapsulated liquids is disclosed in U.S. Pat. No. 5,154,927. Using these methods the total volume of liquid which can be encapsulated is very small, being approximately 0.1 ml for a standard sized piece of gum.

The present invention aims to provide gums in which significantly more liquid (e.g. up to 1.0 ml or more) can be formulated in each piece of gum.

Therefore, it is an object of this invention to provide a chewing gum product giving improved sustained release of active ingredients and one which is particularly suitable for thermolabile biological ingredients and other medicaments some of which may be required to be in liquid solution.

DISCLOSURE OF INVENTION

The invention provides a method of manufacturing a chewing gum comprising the steps of:
 a) entrapping a liquid within a mass of gum;
 b) cooling the gum by an amount sufficient to freeze the entrapped liquid and thereby form entrapped frozen liquid crystals within the gum; and
 c) regulating the temperature of the gum so as to manipulate the size and/or morphology of the frozen liquid crystals, and thereby manipulate the internal structure of the gum to provide a gum having spaces therein of a plate-like or sheet-like shape.

It has been found that by controlling the size and/or morphology of the frozen crystals inside the gum matrix, it is possible to obtain good control of the internal spaces inside the gum. The distribution of an active ingredient in the liquid is thus controllable, and this has a significant impact on the release characteristics of the gum.

Preferably, a step a) comprises comminuting the gum to a particulate form and adding the liquid thereto.

The liquid can thus act as a binder for the particulate gum. The liquid may be an active ingredient in itself, or it may contain an active ingredient (or a flavouring) in solution, suspension or homeopathic dilution. Alternatively, a simple liquid such as water may be added simply in order to use the frozen crystals of water to control the internal structure of the gum. If the water is subsequently removed, one is left with "blanks" which are adapted to absorb a liquid in the internal spaces vacated by the water.

Preferably, the comminution of the gum is achieved by a process selected from jet milling, homogenisation in a suspending liquid, and cryogenic milling.

The operation of a jet mill is well known to those skilled in the art. In jet milling, particle size reduction occurs from collisions between particles driven at high speeds by cold nitrogen gas. As a starting material, commercially available gum base is supplied in particulate form of a size suitable for feeding into a jet mill. Particles whose size is sufficiently reduced exit the mill chamber automatically.

In homogenisation in a suspending liquid, pieces of gum are suspended in a liquid such as a saturated aqueous salt solution. A commercially available homogeniser is used to reduce the gum particles to an extremely fine suspension. The operation occurs at a suitably low temperature to allow the gum to be effectively chopped. As an alternative to a salt solution, any liquid having a low enough freezing point may be used.

In cryogenic milling, the gum is frozen and ground to a suitable size by any known method of comminuting a brittle mass.

Alternatively, step a) may comprise melting the gum, adding a liquid thereto, and forming an emulsion of the liquid in the melted gum.

This method is less preferred as it is unsuitable for substances which are denatured at high temperatures. However, it may be suitable for robust ingredients, or for simple liquids such as water when water is added on its own.

Preferably, step b) comprises blast freezing the gum to a solid state.

Blast freezing is rapid freezing obtained by creating the maximum temperature differential between the unfrozen mass and a freezing surface, thereby achieving the maximum heat flow rate from the freezing mass. When the liquid contains an active ingredient in solution, blast freezing tends to cause the water and solute molecules to take up a much smaller crystal structure relative to those that would be present if freezing was effected at slower rates. The initially smaller crystal structures allow room for more crystal growth when the temperature is varied during annealing (as described below). This in turn allows the water/gum matrix to be better compacted during ice annealing.

Suitably, the gum is frozen to a temperature which is more than 10° C. below the freezing point of said liquid.

Preferably, step c) comprises regulating the temperature of the gum while maintaining the liquid in frozen form.

In particularly preferred embodiments, step c) comprises bringing the gum to a temperature at which the crystals undergo annealing.

During annealing, the frozen crystals grow and bond with one another. In so doing, they generate pressure at the interface with the gum, compressing the pieces of gum together (when the gum has been formed by adhering comminuted gum particles together).

The structure of the crystals generated by annealing determines the distribution of the liquid within the gum. In particular when the liquid comprises water, the ice crystals tend to anneal into sheet-like or plate-like structures which subsequently provide a sustained release of an ingredient contained in the spaces formed during annealing.

Preferably, the annealing temperature to which the gum is brought in step c) is sufficiently warm to cause the gum to exhibit plasticity without allowing the liquid to melt.

At such temperatures, the plasticity of the gum facilitates the crystals annealing together and enables the structure of the gum matrix to be manipulated, which in turn influences the release characteristics of the gum during chewing.

Further, preferably, the temperature to which the gum is brought in step c) is within 5° C. of the melting point of the frozen liquid.

Suitably, the gum is maintained at an annealing temperature for not less than 2 hours.

The process of crystal growth during annealing is relatively slow, and the morphology of the crystals is thus determined both by the annealing temperature and the duration of the annealing step.

In certain embodiments, step c) comprises thawing the liquid and re-freezing the liquid at least once, more preferably at least three times.

This can be referred to as "freeze-thaw texturising" the gum. The individual particles of gum are compressed together with a relatively large force arising from the advancing ice front as the liquid freezes. Repetition of the freeze-thaw cycle gives rise to a gum having a good consistency, and indeed allows the consistency to be accurately controlled.

In preferred embodiments, the method further comprises the step of:

d) removing the liquid from the gum after step c).

In particular, unless it is important for the liquid to be actually present in the finished gum, the preferred finished product will generally be a dry gum. In particular, removal of the liquid will leave behind any suspended or dissolved ingredients, thereby providing a gum in which these ingredients are incorporated within spaces whose size and shape has been determined by the aforementioned temperature control.

If no ingredient is entrapped, then the removal of liquid provides "blanks" of gum which are adapted to absorb a liquid into the spaces vacated during removal of the original liquid. Even if no other liquid is absorbed by the blanks, the texture of the gum will be different from conventional gums, since the gum will be interlaced with internal spaces. Thus, a gum is provided which may be advantageous in and of itself, without any emphasis on the delivery characteristics or any entrapped ingredients. From the point of view of manufacturers, such gums utilise fewer ingredients for a given size piece of gum (i.e. a given volume), because much of the internal volume of the gum is filled with air (or another gaseous substance if desired).

Preferably, step d) comprises subjecting the gum to vacuum-assisted freeze drying.

Freeze drying enables the liquid to be extracted from the gum matrix while leaving the spaces originally occupied by the frozen liquid substantially intact. In general, the removal of liquid by freeze drying opens channels from the internal frozen crystals to the surface of the gum. These channels can be re-sealed by coating the gum or by light compression of the surface of the gum.

In preferred embodiments, the liquid comprises a solvent in which a solute has been dissolved, and the solvent is removed to leave the solute entrapped in the gum.

In alternative embodiments, the method further comprises the step of:

d') sealing the gum with the liquid intact either before or after thawing the gum.

This is most suitable when the gum is to be used to deliver a liquid per se, such as a liquid active ingredient or a homeopathic dilution. The volume of liquid entrapped using this method is substantially greater than in prior art methods of entrapping a liquid in a gum.

According to the invention it is possible to get the powdered gum to absorb about 40% of its own weight without feeling wet. The loaded gum can be pressed into a tablet shape and then dipped into molten gum to form a seal. The sustained release characteristics of the gum can be enhances, by freezing, thawing and re-freezing the loaded gum. The end result is a piece of gum consisting of a gum envelope, enclosing a compressed powdered gum matrix, with a water-based solution in the inter-particulate spaces. As an alternative to dipping the loaded pieces of gum in a molten coating, it is possible to seal the porous surface of the compressed gum granules after the liquid active ingredient has been absorbed. For example one can use brief contact with a hot metal surface to seal the gum pieces.

In a further modification of the method according to the invention the gum is mechanically compressed during steps b) and c).

External mechanical compression adds to the internal pressure generated by ice annealing, and further adds to the integrity of the finished pieces of gum.

Suitably, the liquid added in step a) contains a thermolabile substance.

As indicated above, the invention is particularly suitable for such substances as it allows a gum to be prepared while avoiding the use of any elevated temperatures. Thermolabile substances are denatured at unsuitable temperatures, including many biologically important substances, particularly proteins such as enzymes, antibodies and hormones.

Suitably, the liquid added in step a) comprises a homeopathic preparation.

Homeopathic preparations are made by successive dilutions of an active ingredient, to a point (in many cases) where one would expect no molecules of active ingredient to remain in an average sample. Such medicines are widely used, and are generally administered as a liquid or as a lactose pillule which has absorbed the liquid. The present invention provides for the first time a method of incorporating an active ingredient in aqueous form in a finished sustained release gum without subjecting the liquid to elevated temperatures.

A particularly advantageous application of chewing gum prepared according to the invention is in the area of oral medicine. In oral healthcare there are many clinical indications which would benefit from sustained delivery of therapeutic products from chewing gum, examples of these would include xerostomia (dry mouth syndrome), oral thrush, dental caries, gingivitis, periodontitis and mouth ulcers.

There are many conventional medicines available in different formulations designed to treat these conditions. The application of chewing gum preparations is more advantageous when long-term prophylactic use is desired. Many conventional medicines are unsuitable for prophylactic applications due to long-term side effects. Many biological preparations, which would provide long-term prophylaxis, are heat sensitive and are not easily incorporated into chewing gum using the industry standard process.

Suitably, the liquid added in step a) contains one or more purified constituents of egg.

For example, Irish Patent Specification No. 65218 describes a method of developing hyper-immune egg yolk antibodies against the organisms causing oral thrush, and the contents of this patent specification are incorporated herein by reference. Thus, egg immunoglobulin may be used to replicate the constituents of saliva. It is equally feasible to develop antibodies against any oral pathogen, and to combine these with other constituents of egg such as lysosyme to effectively mimic the protective effect of human saliva which will have wide ranging prophylactic applications in oral medicine.

Accordingly, in preferred embodiments the liquid added in step a) contains one or more constituents having biological activity characteristic of human saliva.

Patients suffering from xerostomia are not only disadvantaged by the discomfort and difficulty of having a dry mouth. Because of the immune activity of saliva, such patients are also highly susceptible to oral infection, which makes the incorporation of immune constituents in a gum particularly advantageous.

Suitably, the liquid added in step a) contains a herbal extract. In preferred embodiments, the herbal extract is *Vaccinium myrtilis* or *Melissa officianalis*.

*Vaccinium myrtilis* is known to have vasoprotective properties in oral applications (see Morazzoni & Bombardelli, *Fitoterapia;* LXVII, No. 1, 1996). Similarly the extract of *Melissa officinalis* is known to have therapeutic properties in viral ulceration of the mouth (see Wolbling & Leonhardt, *Phytomedicine,* 1, 25–31(1994)).

In another aspect, the invention provides a chewing gum comprising a gum matrix having spaces within the gum matrix, characterised in that the size and/or morphology of the spaces is determined during the manufacture of the gum by a change in the size and/or morphology of crystals of an entrapped frozen liquid present during manufacture, and in that the spaces have a plate-like or sheet-like shape due to the formation and growth of ice crystals during manufacture.

Such gums provide for a controlled and sustained release of active ingredient, and as indicated above, they enable a significantly higher dose load to be included (up to 1 ml liquid per 3.1 g piece of gum, as opposed to approximately 0.1 ml in the prior art).

As previously described, in certain embodiments the entrapped frozen liquid present during manufacture has been removed from the finished product.

This provides a gum having a "honeycomb" of internal spaces which give the gum a lighter consistency and an improved mouthfeel.

Preferably, the spaces in the finished product contain a residual material originally dissolved or suspended in said liquid.

In alternative embodiments, the spaces in the finished product contain said liquid in thawed form.

Preferably, the spaces are of an average size greater than the average maximum size of individual liquid volumes which can be incorporated in a gum matrix, due to the use of an annealing step which encourages crystal growth between adjacent crystal structures.

Thus, while only relatively small crystals may be formed during the initial freezing of the gum, annealing enables larger volumes to form by adjacent crystals annealing together.

Preferably, the entrapped frozen liquid present during manufacture is a liquid of a type hereinbefore defined.

A further method of entrapping the liquid in the gum is by creating an emulsion of aqueous drug in a gel of gum base in hexane or cyclohexane or similar suitable solvent. The morphology of the dispersed drug can be fixed by rapid freezing of the emulsion and evaporation of the solvent to deposit gum on the frozen droplets of drug. The resulting particles can then be compressed together to obtain a mass of gum having an entrapped liquid, and this mass can then be subjected to freeze-thaw texturising as described herein. Similarly, particles of liquid-containing gum can be obtained by vacuum-assisted cryogenic spheronisation of drug in a polymer, as described in WO-A-95/22036, the contents of which are incorporated herein by reference.

BRIEF DESCRIPTION OF DRAWINGS

The invention will be further illustrated by the following description of embodiments thereof, given by way of example only with reference to the accompanying drawings, in which.

MODES FOR CARRYING OUT THE INVENTION

Example 1
Preparation of gum powder

A standard confectionery gum base (free of flavours and colourings) was used as the starting material for the preparation of a gum powder. Three different methods were used, each of which will be described in turn. Later Examples demonstrate the formulation of the powder in finished chewing gums.

A: Jet milling

Finely chopped pieces of gum (approximately 10 mm cubes) were chilled to −10° C. in a freezer and fed into the hopper of a jet-mill. The mill was driven by nitrogen gas at −70° C. and particle size reduction was achieved by collision in the mill. Particles which were sufficiently reduced in size were entrained in the stream of gas and exited the mill chamber to be recollected in a cyclone apparatus. Recovered particles averaged 50 μm in size (as measured by microscopy).

B: Cryogenic milling

Finely chopped pieces of gum at room temperature were placed in a porcelain mortar and liquid nitrogen was poured on top of them, (the mortar was pre-frozen to −20° C. as the sudden freezing effect of liquid nitrogen could cause a warm mortar to break or even explode). When the nitrogen had boiled off the brittle gum pieces were easily ground with a pestle to a fine powder, this was allowed to come to room temperature. The powder was shown to absorb water to about 40% by weight.

C: Homogenisation

Chopped pieces of gum were suspended in a saturated salt solution at −5° C. An "Ultra-Turax" (Trade Mark) high speed homogeniser was used to chop the gum pieces to an extremely fine suspension. The suspension was filtered under vacuum and the filtrate re-suspended in water and re-filtered to remove residual salt. The wet filtrate was dried by evaporation at room temperature and further drying effected in a desiccator.

As a useful variation on this process one can leave some salt (or any other hygroscopic substance) in the dried matrix as it considerably improves re-absorption of aqueous active ingredient (provided that the salt and the aqueous active ingredient are compatible).

A suitable alternative to saturated salt is a 50% ethanol: water solution, or glycerol, or any other liquid medium which will not freeze at the reduced temperatures necessary to homogenise the gum solution. Homogenisation may be improved at temperatures of −20° C. or less.

Example 2
Replication of industry standard hot melt process (comparison example only).

Figure 1:
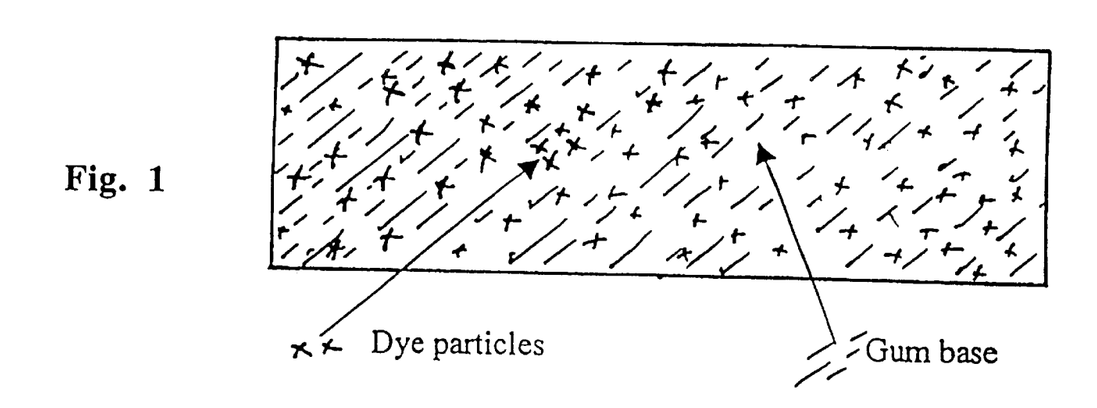
FIG. 1 is a representation of a cross-section of a gum prepared from a powdered gum base and a dye, using a hot melt process.

Red food dye (cochineal) as a dry powder was added to the powdered gum base (prepared according to Example 1A) in an amount of 10% w/w and mixed at 60° C. The molten mixture was spread onto a cool surface and allowed to set at room temperature. Superficially the gum had an intense red colour. The mass was chilled in a refrigerator and broken. The fractured surface was examined under magnification, it was apparent that the dye was dispersed as discrete particles in a uniform gum structure. A representation of the fractured surface is provided in FIG. 1.

Example 3
Replication of dry powder compression process (comparison example only).

Figure 2:
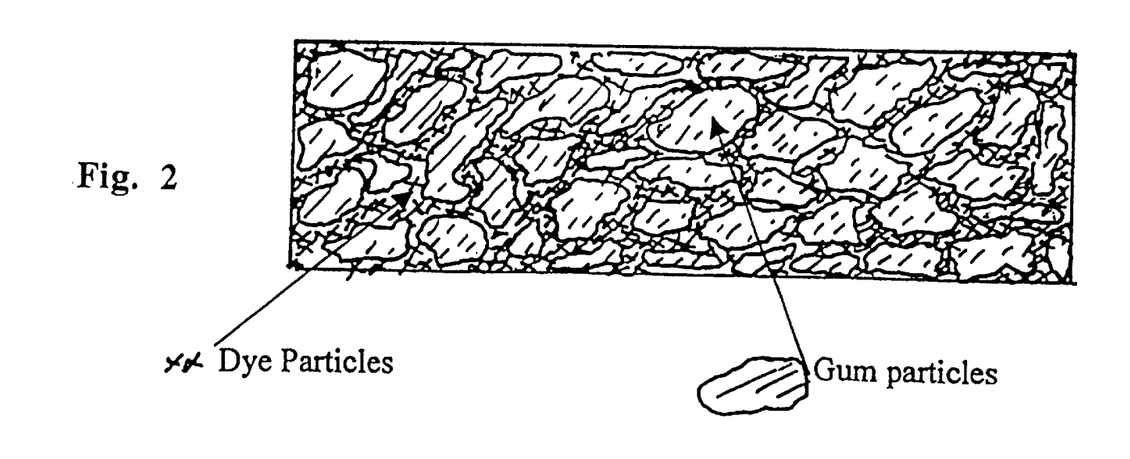
FIG. 2 is a representation of a cross-section of a gum prepared from a powdered gum base and a dye, using a dry powder compression process.

A 10% w/w mixture of cochineal in powdered gum (prepared according to Example 1A) was blended thoroughly. The mixture was compressed into a slab at room temperature. The slab of thus prepared gum was again chilled in a refrigerator and broken. The fractured surface was again examined under magnification, and in this case the red dye was visible as particles coating discrete pieces of the powdered gum. A representation of the fractured surface is provided in FIG. 2.

Example 4
Formulation of powdered gum was liquid solution (comparison example only).

A paste was prepared from the powdered gum of Example 1A by adding a 5% w/v aqueous solution of cochineal in an amount of 10% v/w (0.1 ml solution per 1 g gum). The paste was malleable and relatively easily worked into a slab, by compression between a roller and a surface at room temperature. The cooled slab was cut into individual pieces using a cheese-wire.

The individual pieces felt damp but retained their form. If pieces were placed on blotting paper the dye solution soaked out of the gum pieces into the paper.

Figure 3:
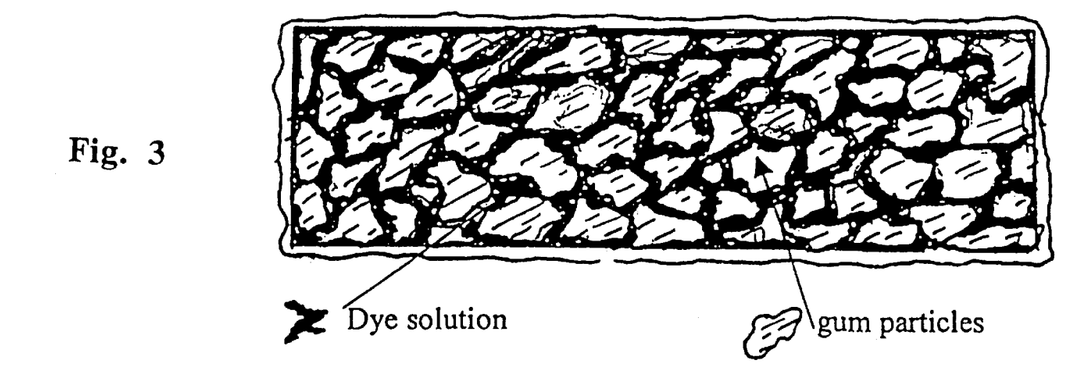
FIG. 3 is a representation of a cross-section of a gum prepared by adding a solution of dye to a powdered gum base.

Individual pieces were coated with molten gum base and allowed to cool. The coated pieces were sliced through with a cheese-wire and examined under magnification. The red dye solution was clearly visible as a thin film coating each piece of the aggregate powder. A representation of the fractured surface is provided in FIG. 3.

Example 5
Formulation of gum according to the invention using freeze-thaw cycle Pieces of gum containing an entrapped liquid solution were prepared according to Example 4.

The gum pieces were placed on a steel tray in a deep freeze at −20° C. for four hours before being removed and allowed to equilibrate at room temperature for 4 hours. The process of freeze-thaw cycling was repeated four times and then the pieces were sliced through with a cheese-wire.

The consistency of the gum matrix had obviously changed as a small amount of dye seeped from the cut surface immediately but further amounts could not be desorbed from the cut surface even by placing the cut section on blotting paper. This indicates that the liquid has for the most part been retained in the gum matrix and thus that a stable gum containing an aqueous solution can be obtained by effecting changes in the morphology of the interstitial liquid-containing spaces in the gum matrix. These changes are brought about by the successive growths of ice crystals during successive freeze-thaw cycles.

Figure 4:
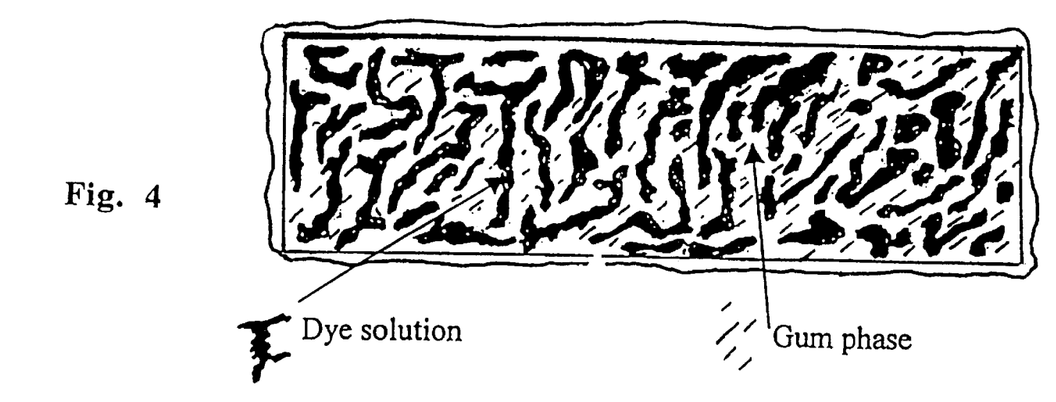
FIG. 4 is a representation of a cross-section of a gum prepared from a powdered gum base and a solution of dye, using a freeze-thaw texturising process according to the invention.

Under magnification the cut surface had a honey-comb or sponge like appearance with dye seemingly trapped in the capillary like matrix: A representation of the cut surface is provided in FIG. 4.

The finished pieces were coated by dipping in a molten gum bath. Alternative coatings which seal in the entrapped liquid can include shellac, gelatine or gum tragacanth.

Example 6

Formulation of gum according to the invention using ice annealing

Pieces of gum containing an entrapped liquid solution were prepared according to Example 4.

The gum pieces were refrigerated to −20° C. and then brought up to −5° C. and held at that temperature for 24 hours to allow ice-annealing to take place. At −5° C. the gum base granules are still relatively plastic in so far as it is possible to distort them under pressure. At −5° C. or thereabouts, the liquid solution was just below its melting, and at this temperature ice crystals grow and re-anneal within the gum matrix.

The process of ice-crystal growth causes substantial pressure to develop at the interface between the ice and the gum and in so doing forces the pieces of gum together, causing them to take up an interconnected lattice structure surrounding the enlarged ice crystals which tend to form sheets during the annealing process. The temperature can be varied for other solutions; in general optimum annealing is achieved by holding the gum at a temperature just below the freezing point of the liquid.

After 24 hours the temperature was again reduced to −20° C. and lyophilisation or freeze-drying commenced. In order to control the rate of drying and the extent of "blowing" in the gum section, no external heat (heating ramp) was used.

The shelves in the drier were maintained at −20° C. for 48 hours, after which secondary drying was effected at +20° C. for 12 hours. The vacuum pressure maintained throughout this 60 hour period was 100 millibars (10 kPa).

An initial scrutiny showed the gum pieces to have an open "woolly" texture, and they were more easily compressed than the other gums described in previous examples. This is considered to be due to the air spaces vacated by the liquid during lyophilisation.

Figure 5:
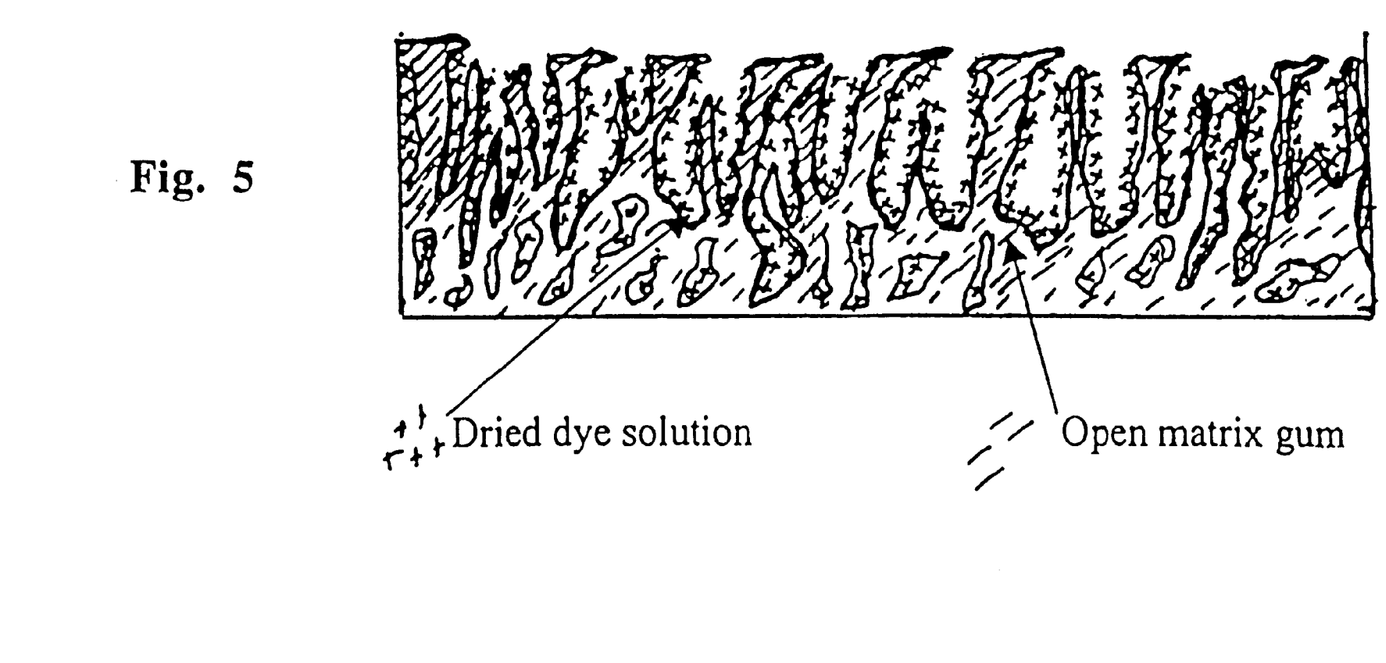
FIG. 5 is a representation of a cross-section of a gum prepared from a powdered gum base and a solution of dye, using an ice annealing process according to the invention.

Under magnification the cut sections of gum were observed to have a marbled appearance with the solute (red dye) deposited in marble-like striations through the gum matrix. A representation of the cut surface is provided in FIG. 5.

The process of lyophilisation is well known to those skilled in the art. A suitable review can be obtained in "Basic Principles of freeze-drying for pharmaceuticals"; A. P. MacKenzie, *Bulletin of the Parenteral Drug Association*, 20, No. 4 (1966). In summary the process consists of freezing a solution (or suspension) and establishing a vacuum over the frozen material to effect sublimation (which may be facilitated by heating the frozen mass). The solvent is sublimed and re-frozen in a condenser operated at temperatures well below that of the subliming frozen solvent.

Using lyophilisation and ice-annealing techniques on the homogenised gum base it is possible to enhance the sustained release characteristics of the final formulation thereby improving the use of such material for oral drug delivery.

The ice annealing procedure can be used to create gum containing liquid active ingredient solutions, which can be retained in the finished product or removed, suitably by lyophilisation. When lyophilisation occurs on a frozen active ingredient solution, the solute (i.e. the active ingredient) is deposited in the gum matrix. Such gum matrices contain dry active ingredient which is readily re-hydrated on chewing. A variation on this technique involves using a simple solvent as the frozen liquid. When the liquid is removed, empty spaces are left behind, i.e. gum "blanks" are created which can be re-hydrated with liquid active ingredient solutions prior to chewing.

The formation of the gum lattice may be facilitated by trapping the liquid paste between steel plates, thus increasing the compression effect during freezing and ice-annealing.

The effect of sublimation in the gum matrix is to cause channels and fissures to open up in the drying mass permitting the escape of water vapour. These channels may be closed in by light compression of the dry matrix without affecting the structure of the formulated gum. If the formulation is intended for absorption of liquid dose into the gum blanks, these fissures will be left open until after re-hydration has been completed.

From the foregoing description it will be apparent to those skilled in the art that the size of the spaces in the gum matrix can be manipulated using freeze-thaw texturising and/or ice annealing prior to drying. Rapid freezing with minimum ice-annealing will create small discrete particles of ice which will blow fissures through the gum as they dry (due to the vapour pressure established during lyophilisation).

Repetitive ice-annealing and freeze-texturising facilitates the growth of larger sheets of frozen solute throughout the gum matrix. In effect the sheets tend to provide channels to a point at or near the surface of the gum. This means that during lyophilisation, there is a minimal amount of channelling through the gum matrix from solvent located in the centre of the gum pieces (the annealing already having provided channels). Thus, there is a minimal effect on the structure and integrity of the gum during lyophilisation, since the sheet-like channels easily open to the surface, and allow the solvent to escape and leave a marbling of dry solute (if present) throughout the gum matrix, which facilitates sustained release of the active ingredient substance.

Some compounds, particularly organic macromolecules, do not form crystals when frozen, i.e. they behave as a glass and retain a certain amount of malleability even at very low temperatures. The inclusion of such "glass formers" in the formulation will enhance the plasticity and ductility of the frozen aggregate.

In comparison to cold milling and dry-mixing, the process described gives improved sustained release characteristics and improved gum texture. The difference is that dry mixing tends to coat the surfaces of the gum particles preventing complete adhesion, this, causes the gum to crumble and fall apart when chewed. The process described herein creates discrete particles or sheets of solute within the gum matrix presenting clean gum surfaces, which re-adhere to each other quite easily.

Example 7

Comparison of lysosyme-containing gums

Lysosyme is a constituent of egg white and purified extracts are readily available for use in the food industry. The enzyme has anti-microbial activity as it catalyses the hydration of murein in bacterial cell walls. The assay procedure involves measuring the spectrophotometric absorption change at 450 nm over time when a solution of enzyme and *Micrococcus lysodecticus* is incubated at 30° C.

A first gum was prepared according to Example 6, but the cochineal was replaced by lysosyme powder added to the gum powder in an amount of 6% w/w.

A second gum was prepared using the hot melt procedure of Example 2, and again replacing cochineal with a 6% w/w solution of lysosyme in gum powder.

Figure 6:
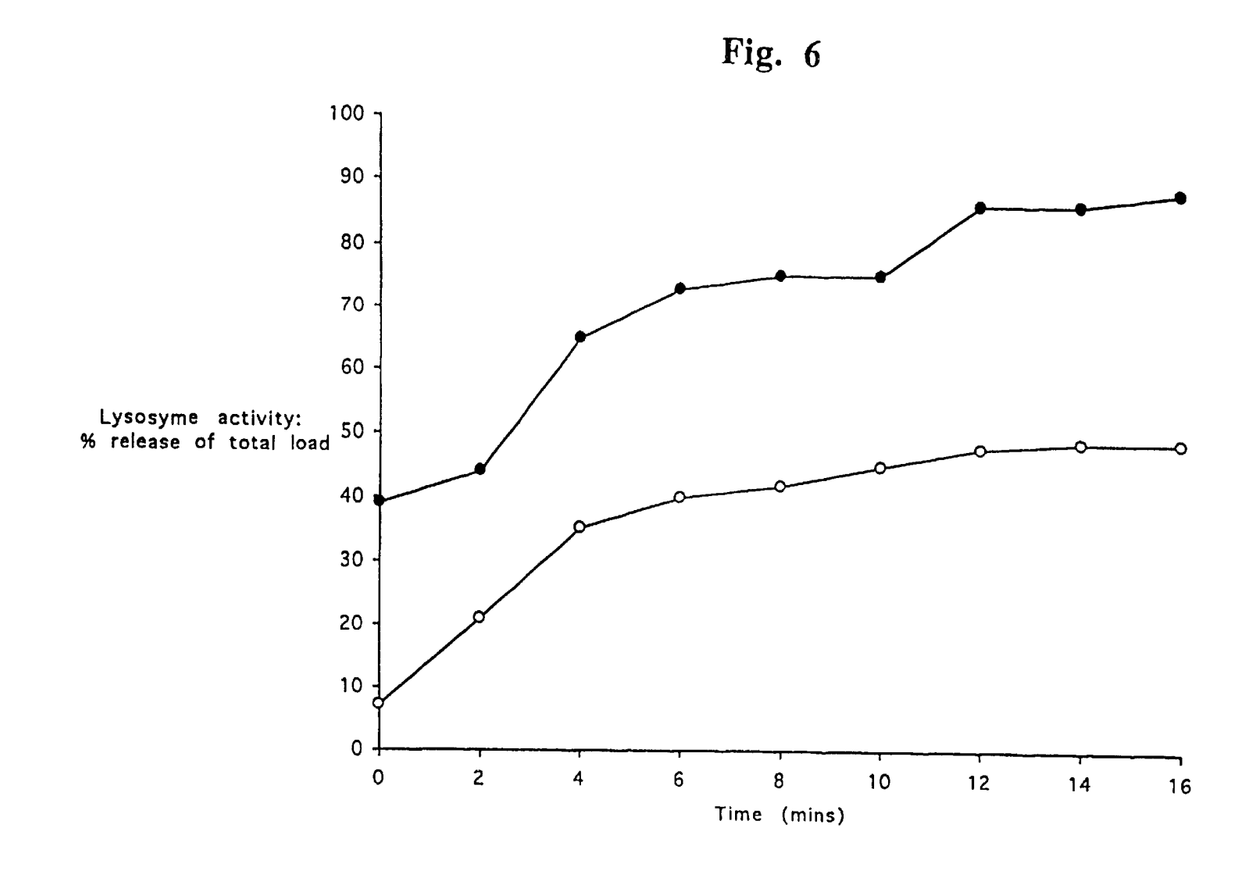
FIG. 6 is a comparative graph illustrating the different release rates over time for gums prepared according to Examples 2 and 6, respectively, but with the dye replaced by lysosyme.

The release rate of both gums was measured over time using a chewing gum dissolution apparatus similar to that described by Rider et al., "Pharmaceutical Research", Vol. 9, No. 2, 1992, and the results are plotted in FIG. 6, which shows the cumulative percentage release of the total load from each gum over a period of 16 minutes. In FIG. 6, the closed circles represent the gum prepared according to the invention, while the open circles represent the hot melt gum.

The chewing gum dissolution apparatus is used to simulate the release of active ingredient by a chewing action into a fluid bath. The assay procedure described above is then used to measure the amount of enzyme at different times. It can be seen from FIG. 6 that the gum according to the invention provided a significantly greater release than from a conventionally prepared gum, and this release was sustained over a fifteen minute period.

It should be noted that although the Examples given above demonstrate the use of the method according to the invention in which the gum is initially frozen to −20° C., much lower initial temperatures are contemplated when the procedure is carried out on a large scale. This is because if the gum is subjected to a temperature of e.g. −50° C. or −100° C., the increased temperature difference between the gum and the surrounding environment will cause more rapid freezing of the gum, and hence will cause the entrapped liquid to form smaller crystals which can be manipulated using freeze-thaw texturising as required.

What is claimed is:

1. A method of manufacturing a chewing gum comprising the steps of:
   a) Entrapping a liquid within a mass of gum;
   b) cooling the gum to freeze the entrapped liquid and thereby form entrapped frozen liquid crystals within the gum; and
   c) regulating the temperature of the gum by using at least one of freeze-thaw texturising or ice annealing to manipulate at least one of the size or morphology of the frozen liquid crystals, and thereby manipulate the internal structure of the gum to provide a gum having spaces therein of a plate-like or sheet-like shape, the spaces being of average size greater than the average maximum size of individual liquid volumes which can be incorporated in a gum matrix, and such that, in use, chewing of the manufactured gum results in a sustained release of the contents of the plate-like or sheet-like spaces.

2. A method according to claim 1, wherein step a) comprises comminuting the gum to a particulate form and adding the liquid thereto.

3. A method according to claim 2, wherein the comminution of the gum is achieved by a process selected from jet milling, homogenisation in a suspending liquid, and cryogenic milling.

4. A method according to claim 1, wherein step a) comprises melting the gum, adding a liquid thereto, and forming an emulsion of the liquid in the melted gum.

5. A method according to claim 1, wherein step b) comprises blast freezing the gum to a solid state.

6. A method according to claim 1, wherein the gum in step b) is frozen to a temperature which is more than 10° C. below the freezing point of said liquid.

7. A method according to claim 1, wherein step c) comprises regulating the temperature of the gum while maintaining the liquid in frozen form.

8. A method according to claim 7, wherein step c) comprises bringing the gum to a temperature at which the crystals undergo annealing.

9. A method according to claim 8, wherein the annealing temperature to which the gum is brought in step c) is sufficiently warm to cause the gum to exhibit plasticity without allowing the liquid to melt.

10. A method according to claim 8, wherein the annealing temperature to which the gum is brought in step c) is within 5° C. of the melting point of the frozen liquid.

11. A method according to claim 8, wherein the gum is maintained at an annealing temperature for not less than 2 hours.

12. A method according to claim 1, wherein step c) comprises thawing the liquid and re-freezing the liquid at least once.

13. A method according to claim 12, wherein step c) comprises thawing the liquid and re-freezing the liquid at least three times.

14. A method according to claim 1, further comprising the step of:
   d) removing the liquid from the gum after step c).

15. A method according to claim 14, wherein step d) comprises subjecting the gum to vacuum-assisted freeze drying.

16. A method according to claim 14, wherein the liquid comprises a solvent in which a solute has been dissolved, and wherein the solvent is removed to leave the solute entrapped in the gum.

17. A method according to claim 1, further comprising the step of:
   d') sealing the gum with the liquid intact either before or after thawing the gum.

18. A method according to claim 1, wherein the gum is mechanically compressed during steps b) and c).

19. A method according to claim 1, wherein the liquid added in step a) contains a thermolabile substance.

20. A method according to claim 1, wherein the liquid added in step a) comprises a homeopathic preparation.

21. A method according to claim 1, wherein the liquid added in step a) contains one or more purified constituents of egg.

22. A method according to claim 1, wherein the liquid added in step a) contains one or more constituents having biological activity characteristic of human saliva.

23. A method according to claim 1, wherein the liquid added in step a) contains a herbal extract.

24. A method according to claim 23, wherein the herbal extract is *Vaccinium myrtilis*.

25. A method according to claim 23, wherein the herbal extract is *Melissa officianalis*.

* * * * *